(12) United States Patent
Rousseau

(10) Patent No.: US 7,943,100 B2
(45) Date of Patent: *May 17, 2011

(54) CUVETTE FOR IN VITRO DIAGNOSIS

(75) Inventor: Alain Rousseau, Paris (FR)

(73) Assignees: Immunodiagnostic System France, Pouilly En Auxois (FR); Alain Rousseau, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/662,738

(22) Filed: Apr. 30, 2010

(65) Prior Publication Data
US 2010/0247385 A1 Sep. 30, 2010

Related U.S. Application Data

(62) Division of application No. 11/631,164, filed as application No. PCT/FR2005/001830 on Jul. 18, 2005.

(51) Int. Cl.
G01N 21/03 (2006.01)

(52) U.S. Cl. ..... 422/401; 422/560; 422/566; 435/288.4; 435/305.2; 436/47

(58) Field of Classification Search ............ 422/401, 422/560, 566; 435/288.4, 305.2; 436/47
See application file for complete search history.

(56) References Cited

U.S. PATENT DOCUMENTS

| | | | |
|---|---|---|---|
| 3,684,452 A | 8/1972 | Bessman | |
| 3,713,985 A | 1/1973 | Astle | |
| 4,123,173 A | 10/1978 | Bullock et al. | |
| 4,695,430 A | 9/1987 | Coville et al. | |
| 4,774,055 A | 9/1988 | Wakatake et al. | |
| 4,785,407 A | 11/1988 | Sakagami | |
| 4,918,984 A | 4/1990 | Martinoli et al. | |
| 5,055,262 A | 10/1991 | Sakagami | |
| 5,175,086 A | 12/1992 | Takekawa et al. | |
| 5,316,726 A | 5/1994 | Babson et al. | |
| 5,350,564 A | 9/1994 | Mazza et al. | |
| 5,380,487 A | 1/1995 | Choperena et al. | |
| 6,106,781 A | 8/2000 | Rosenberg | |
| 6,767,511 B1 | 7/2004 | Rousseau | |
| 2004/0048361 A1 | 3/2004 | Isobe et al. | |
| 2004/0053414 A1 | 3/2004 | Devlin, Sr. | |

FOREIGN PATENT DOCUMENTS

| | | |
|---|---|---|
| EP | 0 325 874 A1 | 8/1989 |
| EP | 0 386 855 A1 | 9/1990 |
| EP | 1 382 392 A1 | 1/2004 |
| JP | U-58-80564 | 5/1983 |
| JP | A 59-147267 | 8/1984 |

(Continued)

OTHER PUBLICATIONS

International Search Report issued in International Application No. PCT/FR2005/001830 on Jan. 11, 2006. Restriction Requirement issued in U.S. Appl. No. 11/631,164 on Mar. 26, 2010.
U.S. Office Action issued May 26, 2010 in related U.S. Appl. No. 11/631,164.
Nov. 12, 2010 Office Action issued in U.S. Appl. No. 11/631,164.

*Primary Examiner* — Lyle A Alexander
(74) *Attorney, Agent, or Firm* — Oliff & Berridge, PLC

(57) ABSTRACT

The device comprises reaction unit cuvettes for different types of tests, a vertical axis rotor which is associated with a rotation drive means and provided with a horizontal gear-teeth crown delimiting radially outwardly open cavities for receiving the reaction unit cuvettes, a device for supplying the gear-teeth crown with the reaction unit cuvettes, a device for supplying cuvettes with analyzable biological liquid samples, stations arranged around the crown for carrying out measurements and/or analysis and an automation for managing the sequences of a desired process for each cuvette.

6 Claims, 8 Drawing Sheets

FOREIGN PATENT DOCUMENTS

Figure 1:
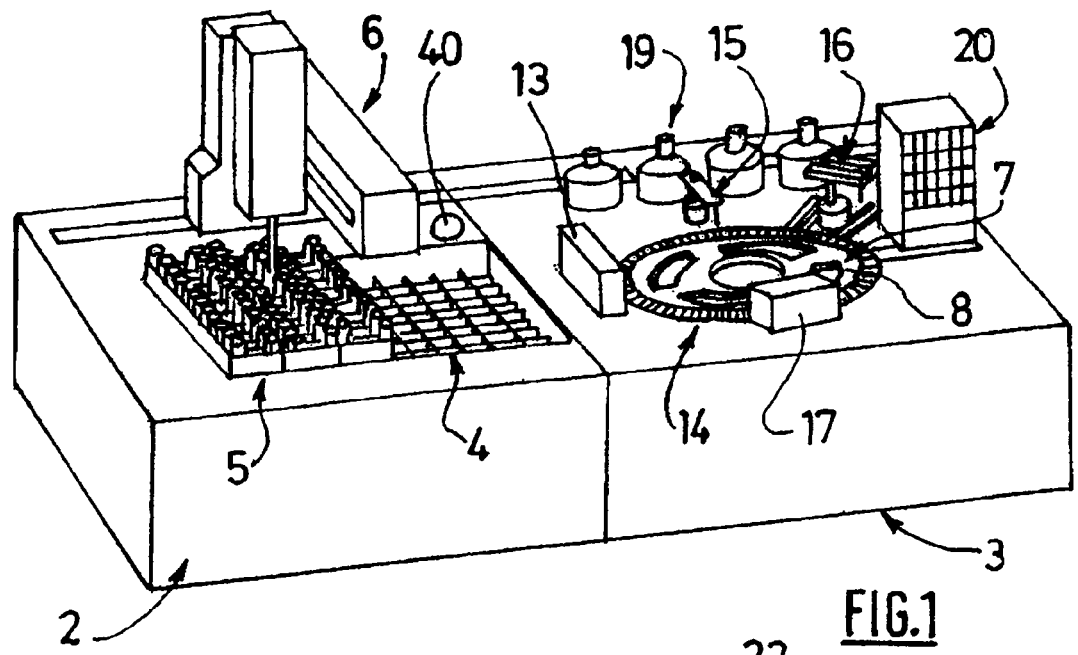

| | | |
|---|---|---|
| JP | A-2-45763 | 2/1990 |
| JP | A-8-43400 | 2/1996 |
| JP | A-11-223633 | 8/1999 |
| WO | WO 88/02866 A1 | 4/1988 |
| WO | WO 92/04978 | 4/1992 |
| WO | WO 92/14550 A1 | 9/1992 |
| WO | WO 93/02364 A1 | 2/1993 |
| WO | WO 93/03347 | 2/1993 |
| WO | WO 93/15408 | 8/1993 |
| WO | WO 99/64839 | 12/1999 |

CUVETTE FOR IN VITRO DIAGNOSIS

This is a Division of application Ser. No. 11/631,164 filed Dec. 29, 2006, which is a National Stage of Application No. PCT/FR2005/01830 filed Jul. 18, 2005. The disclosures of the prior applications are hereby incorporated by reference herein in their entirety.

The present invention relates to an automatic analytical device for in vitro diagnosis, and also to a unit cuvette used by this device.

In vitro diagnosis can be subdivided into several disciplines that use different measurement technologies. The latter consist in quantifying an analyte, in measuring an enzymatic activity, etc., in an aqueous biological medium, i.e. tests which are carried out on serum, plasma or other media and in which the measurement is the result of a reaction process that uses reagents, the medium to be assayed, and one or more containers or consumables used for the reaction. An instrument, a piece of equipment or a machine can automate the process of sampling and distributing the products concerned, can carry out the measurements on demand, performs the calculations and the data processing and renders the results in the desired form.

In particular, the present invention relates, in general, to the following technologies for performing a measurement:
  clinical chemistry or biochemistry tests that are carried out using blood serum or other aqueous biological media and in which the principle of measurement used is essentially spectrophotometry.
  immunoassays carried out according to different technical methods:
    RIA, IRMA, which are assays using radioisotopes and that cannot be readily automated,
    latex agglutination tests,
    ELISA, EIA, the measurement being carried out by spectrophotometry, fluorescence or CLIA by luminescence.
  Plasma coagulation tests that themselves are a result of several technologies, but that essentially consist in measuring the time taken for a clot to form.

All these analyses have in common the fact that they make use of:
  a sample tube: serum, plasma or the like, of which it is desired to measure, evaluate or assay one or more analytes,
  one or more reagents which have the function of revealing the analytes sought,
  an automatic instrument that carries out the analytical process specific to each analyte according to a procedure that is precise in terms of quantity and over time,
  solid consumables (cuvettes, tips, etc.) to serve as a reactor,
  ancillary reagents, for participating in the precise and exact sampling of the specimens and reagents, for decontaminating and rinsing,
  a man-machine interface that makes it possible to request transactions, loadings, requests, validations, etc., the object of which is the charter of the results of the file processed.

Most commonly, automatic analytical instruments are specialized for biochemistry, others for immunology and coagulation.

Some instruments are designed to give measurements in several disciplines, but are either extremely complex, resulting in high costs, or are only sequentially multi-purpose, i.e. they cannot process analyses file by file, and they require manual interventions for switching from one measurement technology to the other.

Laboratories therefore have several instruments that are sometimes connected to one another by systems for conveying specimen tubes.

It remains the case that each instrument, whether it is in a system or not, has its software, its consumables, and its own specific material architecture that requires specific training for users and that means greater expenditure must be made in the laboratories.

The present invention makes it possible to combine, in a single device, all the abovementioned techniques used in laboratories and falls resolutely into line with the reduction of health costs, and with the requirement for laboratories to have simpler equipment, requiring a reduced training period for personnel. It is not uncommon to see, in a hospital laboratory, given the organization in teams and the rotation of personnel, a piece of equipment used by about fifty people who are obviously not all optimally trained on the instruments that they are using. The consequences in terms of system reliability, and of handling errors that can impair the quality of results and cause diagnostic errors and increased running costs, are considerable.

The disciplines of biochemistry, immunology and coagulation make use of the same instrument functions and of similar products, but they show different requirements in terms of the measurement processes.

For example, biochemical tests are short: a few minutes are sufficient from the taking of samples of the specimens and reagents to the end of the spectrophotometric measurements.

Immunoagglutination tests are also the result of this type of process and they are very generally part of the lists of tests available on the pieces of biochemical apparatus. Unfortunately, their sensitivity is limited and they only cover a modest part of immunological needs.

On the other hand, immunoassays carried out with other methods are comparatively long. In addition, the conventional spectrophotometric measurement for these sandwich-type immunoassays does not make it possible to obtain sufficient sensitivity. It is necessary to use fluorescence or preferably luminescence in order to obtain the desired sensitivities. The measurement technology in this case does not use the means used in biochemistry.

In coagulation, the difficulty also comes from the measurement technology, but for different reasons. Specifically, what is measured is the time between the introduction of a triggering reagent and the appearance of the clot. This time can vary, depending on the tests, from a few seconds to several minutes. During this time, the reactor in which the series of enzymatic reactions that results in fibrin polymerization and clot formation takes place must be constantly under observation in order to be able to provide an accurate result to within one tenth of a second. When a measurement is initiated, it is not therefore possible to predetermine the end of the process since this is precisely what one wishes to measure.

It is now easier to understand why it is difficult to bring these measurement technologies together on the same piece of equipment and also the choices made up until now:
  analyzers that work sequentially per discipline in order to do away with the problems of temporarily incompatible processes,
  hybrid machines that result from the juxtaposition of several pieces of specialized equipment per discipline.

Various types of measurement and/or of analysis have already been grouped together in the same device. Document EP 0325874 describes a system that allows two types of measurement:

a mechanical measurement of clot formation, a photometric or densitometric measurement for measuring phenomena that are the result of hemostasis but that are not reflected by coagulation.

In hemostasis, the parameters are essentially those that can be quantified by effective coagulation, but others are parameters that come under biochemistry or immunology (latex), and that can, moreover, be measured on biochemical analyzers: ATIII, plasminogen, D dimer, etc.

Now, in order to completely satisfy a hemostasis department in a hospital, it was advisable to offer all the parameters of this discipline on the same piece of equipment and therefore to be able to carry out simply, on this same piece of equipment, tests for which the processes are very different in nature.

This problem is managed by using reactors called unit cuvettes that can each have a different process managed independently.

However, the instruments still remain quite complex, due to the fact that the transport of these cuvettes inside the automated devices is problematic (WO 99/64839) or induces the addition to the machine of a cuvette distributor that also makes the equipment more complex or is detrimental to its compactness and to its reliability.

In addition, the use of individual cuvettes does not on its own provide a solution to the management of very different analytical processes. Specifically, measurement processes that are long (immunology) or that require the continual observation of the phenomenon to be measured (coagulation) must not constitute bottlenecks for tests where the process is rapid (biochemistry).

Finally, the multiplicity of tests on the same piece of equipment makes the questions of contamination between tests and between specimens acute. Equipment validations become difficult and problematic. Washing systems that consume very large volumes of detergent liquids and of decontaminating fluids are used. The amounts of effluents become difficult to manage.

The basis of the invention is the production of an automatic analytical device which is multi-purpose but simple and therefore relatively inexpensive to manufacture and to maintain and the running costs of which are substantially lower than those of the current automatons, with, as a consequence, a reduction in the number of machines per laboratory, thus contributing to a reduction in public health spending.

To this effect, the device to which the invention relates comprises:

a model of reaction unit cuvettes for different types of tests, using different measurement technologies, a vertical-axis rotor which is associated with rotation drive means and provided with a horizontal toothed crown wheel, delimiting, radially outwardly, open cavities for receiving unit cuvettes, a device for supplying the toothed crown wheel with reaction unit cuvettes, a device for supplying the cuvettes with specimens of biological liquid to be analyzed, stations arranged around the crown wheel, for carrying out measurements and/or analyses, some of these stations comprising means for emptying/filling the cuvettes for carrying out a measurement and/or an analysis at the station, outside the crown wheel, an automaton controlled by on-board software for managing the sequences of the desired process for each cuvette.

Advantageously, the device comprises means for maintaining the temperature of the cuvettes at a given level.

Advantageously, the means for maintaining the temperature of the cuvettes consist of an upwardly open U-shaped stationary toroidal piece delimiting, between the toothed crown wheel and the torus, a space that is temperature-regulated by virtue of the thermostatting of the torus carried out by known means. In addition, the torus comprises a radial opening in its outer branch opposite each station, where a cuvette is introduced or withdrawn.

The temperature at which the toroidal guidance piece is maintained is advantageously 37° C.

It follows from the above characteristics that the cuvettes can be very simply disengaged from the toroidal piece, at a station, so as to undergo a process of analysis of their content at this station. The cuvette can remain for the amount of time desired for said analysis, without blocking the movement of the drive crown wheel which simultaneously ensures the transfer or the maintaining in position of other cuvettes at other measurement and analysis stations. Thus, the analyses requiring a relatively long period of time can be carried out in background time, at a specific station, whereas other instantaneous analyses are carried out at other stations.

This is made possible, in this device, insofar as the toroidal piece comprises radial openings in its outer branch, these openings being positioned to coincide with the openings of the cavities of the drive crown wheel, allowing transfer of the cuvettes by means of a small conveyance between the cavity of the crown wheel and an analysis station.

According to one characteristic of the invention, the means for filling/emptying the cuvettes consist of a linear actuator comprising an electric stepper motor having screw-to-screw device forming a cylinder, optical sensors being provided for determining the position of the actuator.

According to one possibility, the actuator comprises, at the end of the shaft, a paddle forming a push rod.

According to another possibility, the actuator is a dual-acting actuator and comprises, at the end of the shaft, an upwardly open U-shaped actuating piece, normally located in the cuvette displacement path.

Depending on the case, the actuator is mounted on the U-shaped toroidal piece, or the actuator is mounted on the support of a station placed outside the cuvette drive crown wheel.

Another characteristic of the invention is the modularity of this device. It comprises a combination of modules distributed around the drive crown wheel. These combinations are produced according to the specificity of the instrument. By way of nonlimiting example: spectrophotometric reading module, fluorescence reading module, sedimentation and washing module, luminescence reading module, module comprising at least one station for measuring coagulation, reagent addition module, cuvette evacuation module.

Advantageously, the device comprises at least one station for measuring coagulation, comprising a retractable optical fork in which a cuvette is intended to be housed, and comprising, on one branch of the fork, at least one light-emitting diode and, on the other branch of the fork, at least one detection photodiode.

According to one embodiment, the fork has a separation substantially equal to the large transverse dimension of a cuvette, a reading of absorbance between the light-emitting diode and the photodiode being carried out along this large dimension of the cuvette.

The light-emitting diode may be a component that integrates several diodes having various wavelengths, and these diodes are periodically switched so as to allow the formation of a clot to be optically monitored at several wavelengths.

Advantageously, the device comprises at least one well for rinsing and/or decontaminating sampling and distribution needles, comprising a source of decontaminating liquid, the rinsing being carried out by a pulsed and then suctioned flow.

These arrangements allow successive dilutions of the liquid with which the needle is in contact.

According to one embodiment, the device comprises a station for positioning a cuvette in which the dilutions or aliquots are made.

This device makes it possible:

1) to carry out spectrophotometric measurements on the cuvettes when the rotor positions them between the elements of the known device of spectrophotometric measurement,
2) to evacuate from the rotor, into a waste container, the cuvettes that have completed their spectrophotometric measurement cycle,
3) to deposit a given volume of a solution containing a fixed concentration of magnetic nanoparticles of diameter between 100 nm and 900 nm, which are characterized particles functionalized with streptavidin or avidin, into the cuvettes which are the subject of an immunological measurement,
4) to remove from the rotor, after a programmed incubation time, the cuvettes that are the subject of an immunological measurement and to insert them into a magnetic sedimentation and washing module and then to reintegrate the cuvettes into the rotor,
5) to remove the cuvettes from the rotor that have previously been treated in the sedimentation and washing module, to insert them into a module for developing and reading the luminescence, and then to evacuate them, after the measurement, into a waste container,
6) to remove the cuvettes, after a programmed incubation time, which cuvettes have received plasma and, if necessary, one or more coagulation reagents, to position them in one or more measuring cells such that the device B can deposit therein the triggering reagent specific to the reaction under consideration, each cell having optical means for detecting the formation of the clot by absorbance, and then to evacuate them into a waste container,
7) to remove the cuvettes into a dedicated cell or a cell that can be used for measuring coagulation in order to distribute serum or plasma into this cuvette so as to make dilutions or aliquots when the analyzer is able to pierce stoppers of specimen tubes (vacuum sampling tubes).

The device also makes it possible to manage this functional assembly automatically by means of on-board software, which manages the sequences of the process desired for each cuvette.

The device also makes it possible to rinse and decontaminate the needles and tubing in contact with the reagents and (or) the biological specimens.

The toothed crown wheel is a device that makes it possible both to displace the cuvettes and also to carry out measurements in biochemical tests. The crown wheel has a sufficient number of cavities to be able to manage at the same time all the cuvette transfers and the reaction incubations of all the disciplines in order to obtain the desired specimen processing rates.

Analytical devices must have processing rates that are adapted to the needs of laboratories, in which the number of files to be processed per day can range from a few tens to a few hundred, or even a few thousand specimens. Automatic systems that interconnect machines designed for different technologies and disciplines were mentioned above. These systems are without doubt the right answer for laboratories that process quantities of several hundred or thousand tubes per day, but large equipment of this type, which represents a considerable expenditure, cannot be justified for laboratories that process smaller numbers of files. An object of the invention is therefore to make it possible, for a reasonable cost, to have access to equipment that has the advantages of an automatic modular management laboratory system without, moreover, having the drawbacks of said systems of cost, complexity and amount of space taken up.

The invention makes it possible to produce a unified laboratory bench top for biochemistry, immunology and coagulation.

The invention is not particularly directed at large laboratories that process more than 200 specimens a day. It is supposed to provide the ideal piece of equipment for small and medium-sized laboratories, for emergency laboratories, or for research laboratories.

For example, a laboratory corresponding to this description could have the following to process per day:

300 biochemical tests,
80 hemostasis tests,
40 immunology tests.

In order for the equipment to meet demand, it must be possible for about 80% of these daily quantities to be processed within a period of two hours.

The rates of such a piece of equipment should therefore be, overall, greater than 170 tests/hour.

The calculation shows that the rates should therefore be, for the various disciplines:

200 tests/hour for biochemistry,
120 tests/hour for coagulation,
60 tests per hour for immunology.

If the average process time is five minutes for biochemistry and coagulation, and 30 minutes for immunology, this means that the equipment must manage, in parallel:

17 biochemistry tests,
10 coagulation tests,
30 immunology tests.

That is to say a total of 57 tests.

If the rate must be doubled for biochemistry and coagulation, then it will be necessary to manage, in parallel:

34 biochemistry tests,
20 coagulation tests,
30 immunology tests.

That is to say a total of 84 tests in parallel.

In the device of the present invention, a crown wheel having 90 slots makes it possible to handle these two types of configuration.

The processing rate will be fixed by the capacity of the known devices for pipetting the samples and the reagents and by the processing times for the tasks dedicated to the satellite modules.

The present invention also relates to a unit cuvette for an analytical device as described above, characterized in that it comprises means of attachment, in a first direction, to at least one other unit cuvette and means of attachment, in a second direction, substantially perpendicular to the first, to at least one other unit cuvette.

Advantageously, each cuvette, made of a transparent plastic compatible with the various reactions that it may receive, has a lower part of parallelepipedal shape.

It should be noted that the analysis is carried out in the parallelepipedal lower part of the cuvette.

According to one embodiment, the cuvette comprises a cuvette bottom which has a low point.

This shape makes it possible to suction out the liquids with a very small dead volume and to facilitate washing of the magnetic particles.

Advantageously, the parallelepipedal lower part of the cuvette extends upwards by means of a tapered upper part that opens out upwards.

This characteristic makes it possible to increase the rinsing volume or the reaction volume.

According to one embodiment, the means of attachment of the cuvette according to a first direction comprise at least one downwardly open hook positioned on one of the edges of the upper part of the cuvette.

Advantageously, the width of the cuvette in the zone comprising the hook is equal to the width of a cavity of the toothed crown wheel.

This upper hook forming a tongue therefore makes it possible, firstly, to block the cuvette inside a cavity of the drive crown wheel and, secondly, to attach several cuvettes so as to form a cuvette line.

According to one embodiment, the means of attachment of the cuvette according to a second direction comprise two rims, one of which forms an upwardly open hook and the other of which forms a downwardly open hook, the upwardly open hook of one of the rims being able to slot into the downwardly open hook of the rim of a neighboring cuvette, the hooks being positioned on the base of the cuvette, along its two edges orthogonal to the upper edge equipped with a hook.

These rims make it possible to attach the cuvettes to one another, in a direction perpendicular to the direction of attachment obtained using the hooks of the upper part. It is therefore possible to attach cuvettes to one another so as to form plates. In addition, the rims make it possible to have overall dimensions of the cuvettes that are the same in their upper parts and in their lower parts such that, when assembled together, the cuvettes constitute a planar plate. This makes it possible to order the cuvettes so that the cuvette distribution device is simple, compact and reliable.

According to an advantageous characteristic of the invention, aimed at automation of the process, the device comprises a magazine for storing the cuvettes in several stages of plates, each of which consists of cuvettes assembled along two perpendicular directions, the magazine comprising means for forming a line of cuvettes by downward displacement of an end line and detachment of the cuvettes of this line in relation to those of the neighboring line and means for isolating a cuvette located at one end of a line by displacement of this cuvette transversely to the line, before a further displacement, by means of an actuator, into a cavity of the crown wheel.

The cuvettes are therefore arranged in the form of plates in the magazine, and automatically distributed each as a unit into a cavity of the drive crown wheel.

Preferably, this device comprises an automaton for taking samples of specimens of biological liquid, contained in tubes arranged in a storage zone, and of reagents, and for transferring them into cuvettes arranged in cavities of the drive crown wheel.

In addition, the automaton is connected to a computer that constitutes the man-machine interface, which processes user requests, and sends the requests for tests to be carried out on the specimens located by means of an identifier embodied, for example, by a label with a barcode, and loaded onto the equipment.

The principle of the invention will be clearly understood from the description that follows, with reference to the attached schematic drawings represented, by way of nonlimiting example, an embodiment of the device.

Figure 2:
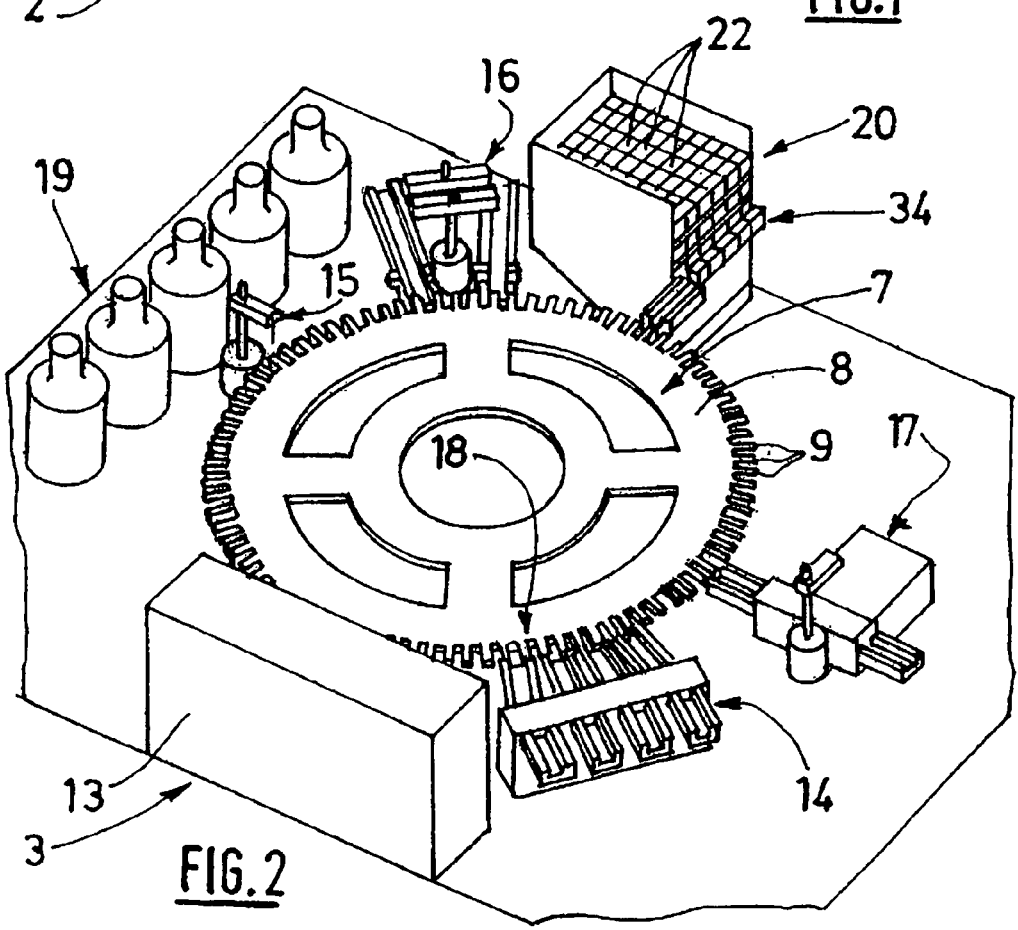
Figure 3:
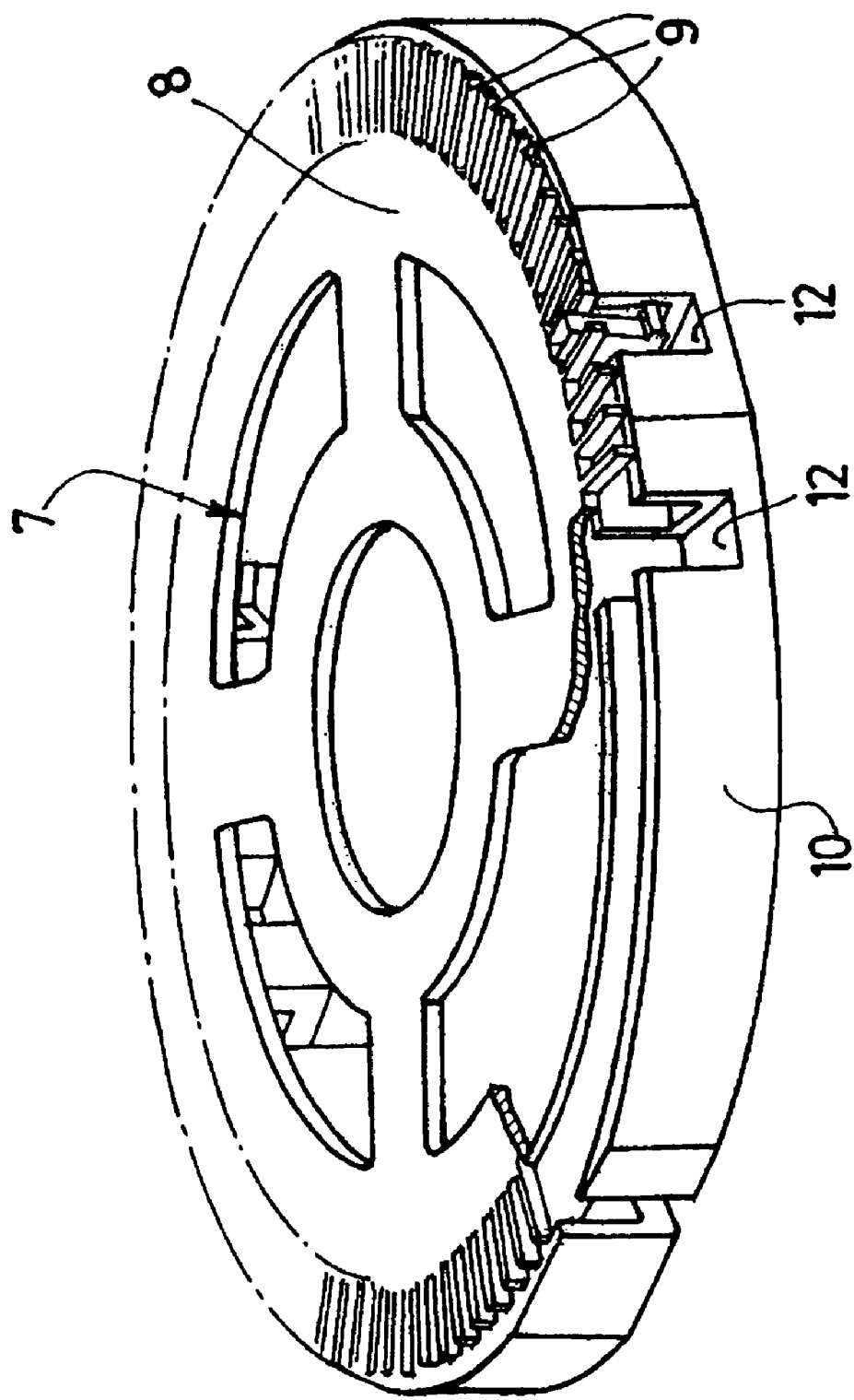
Figures 4, 5:
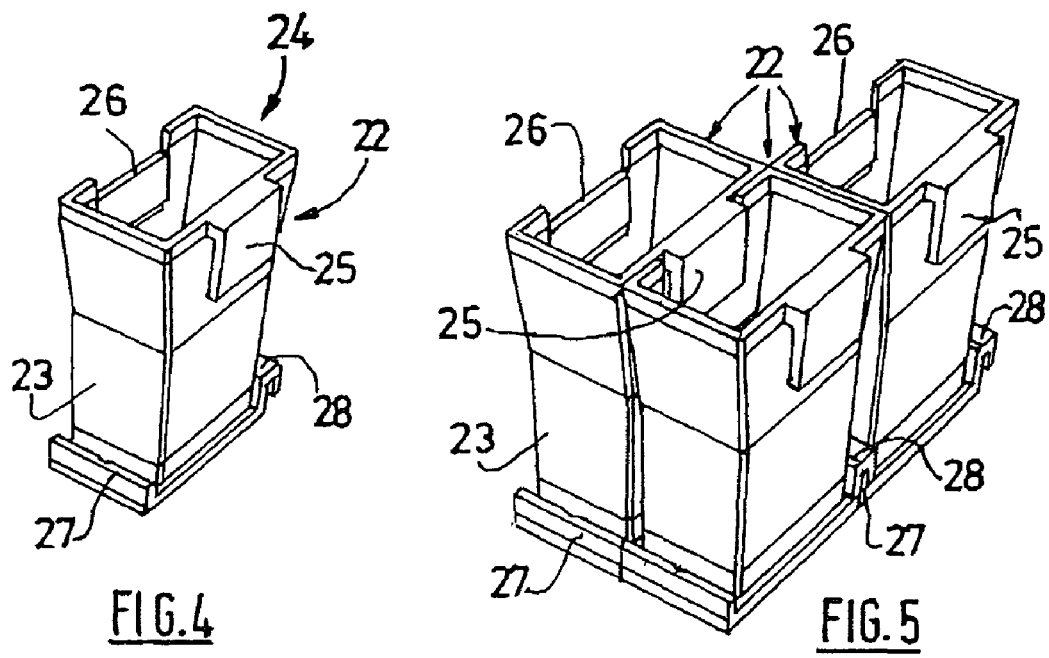
Figure 6:
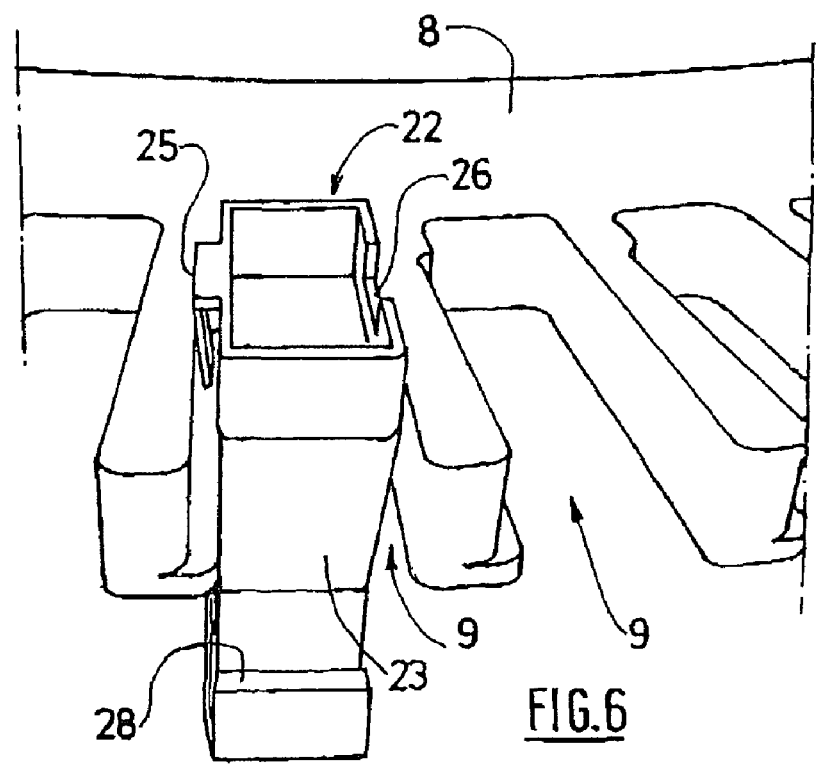
Figure 7:
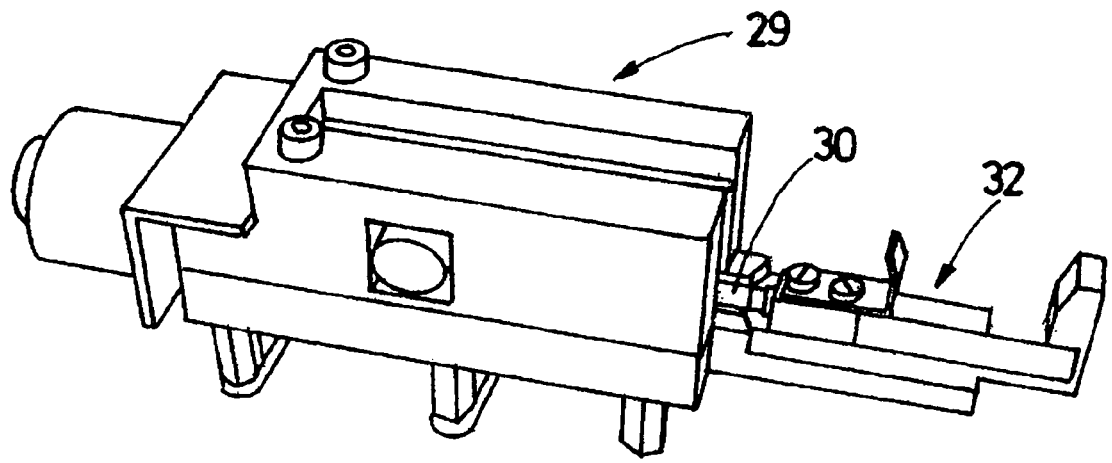
Figure 8:
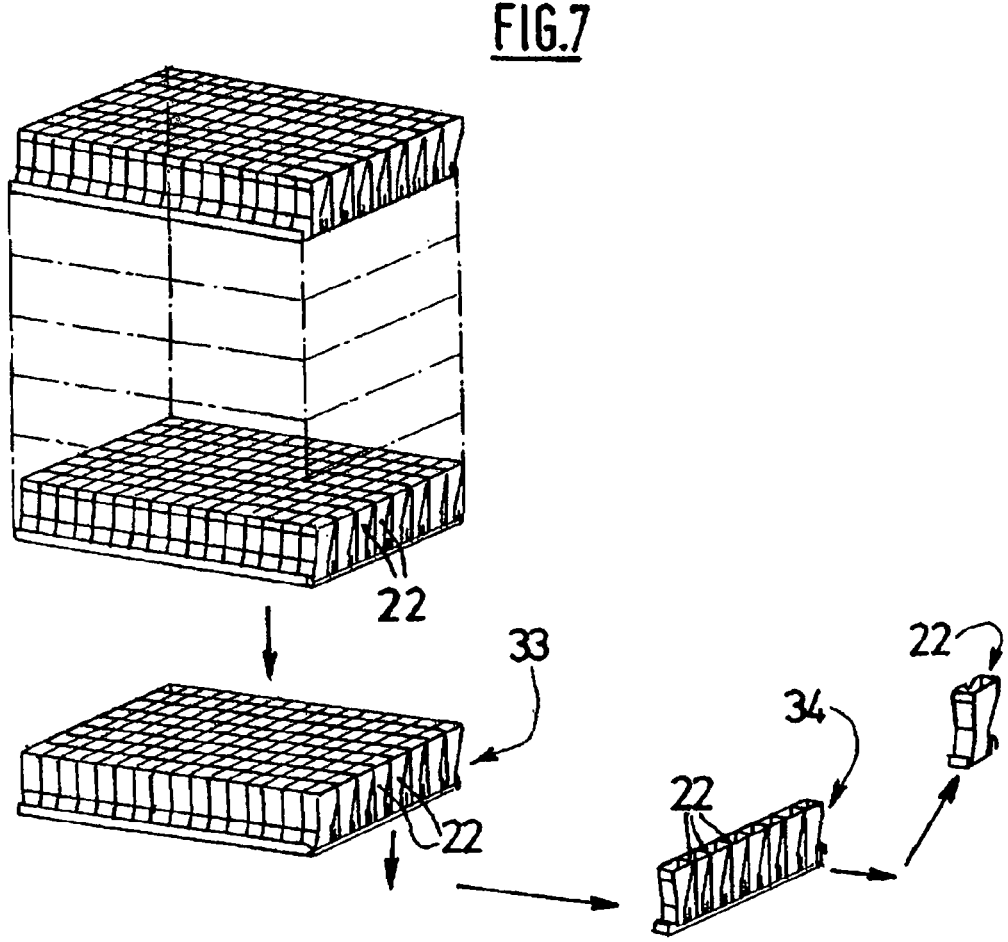
Figure 9:
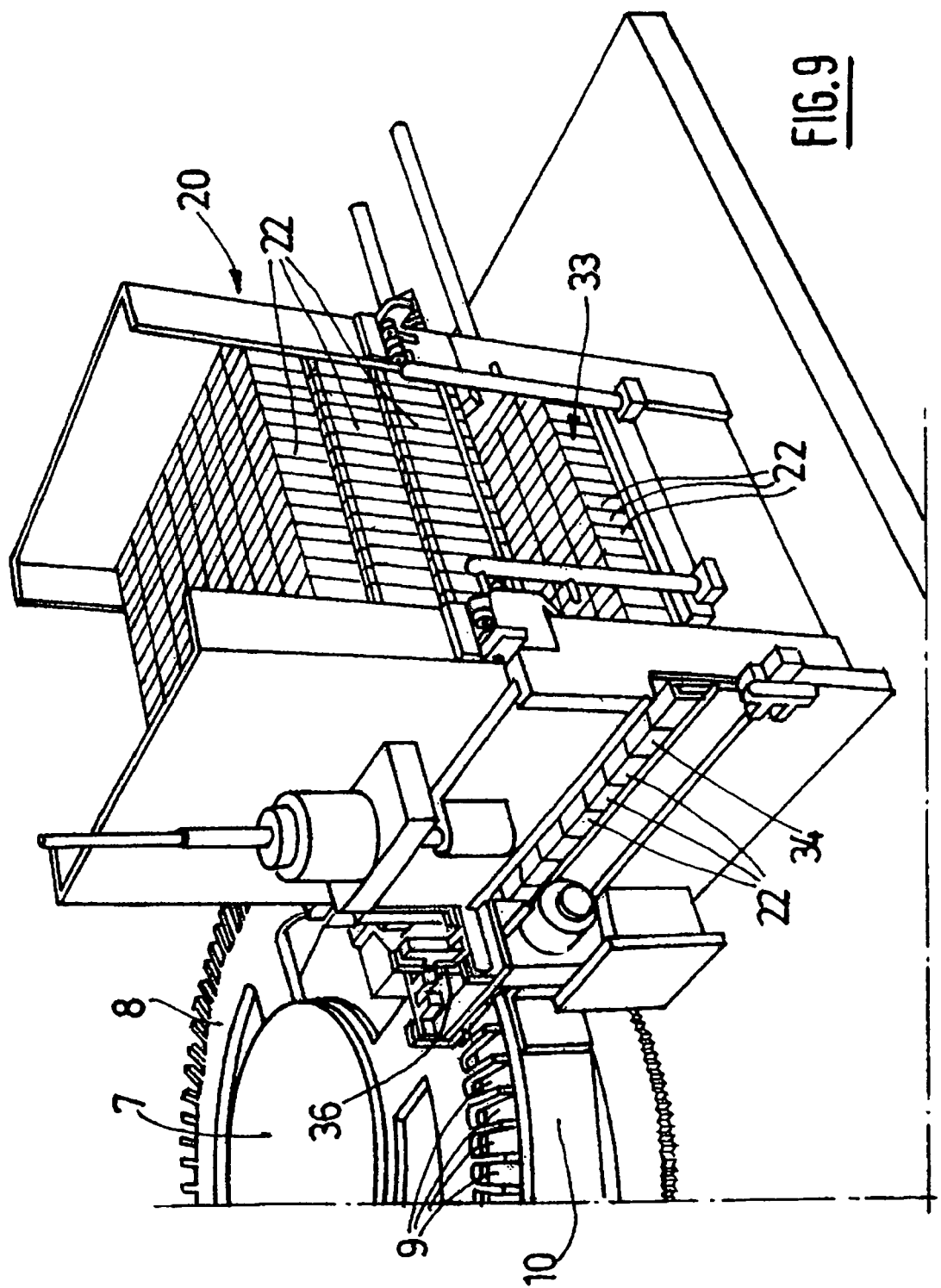
Figure 10:
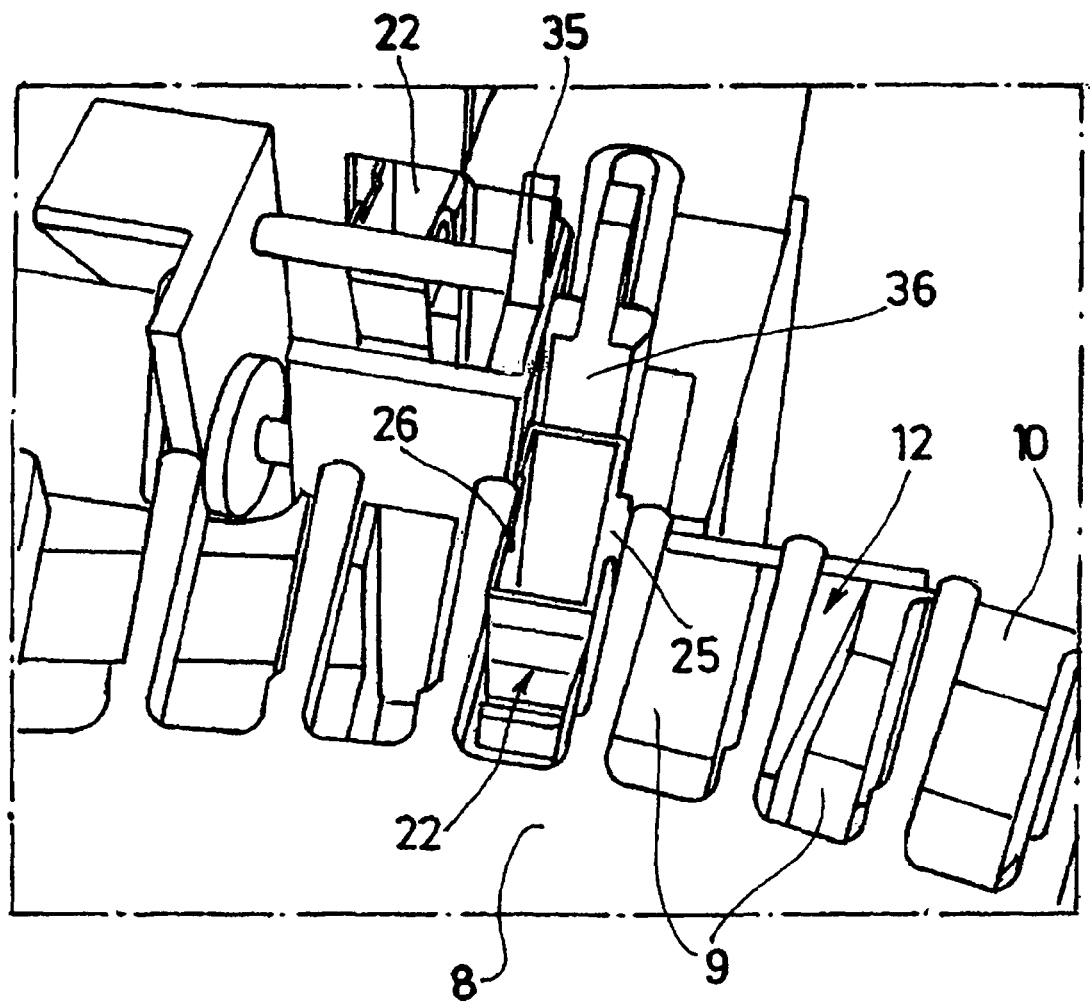
Figure 11:
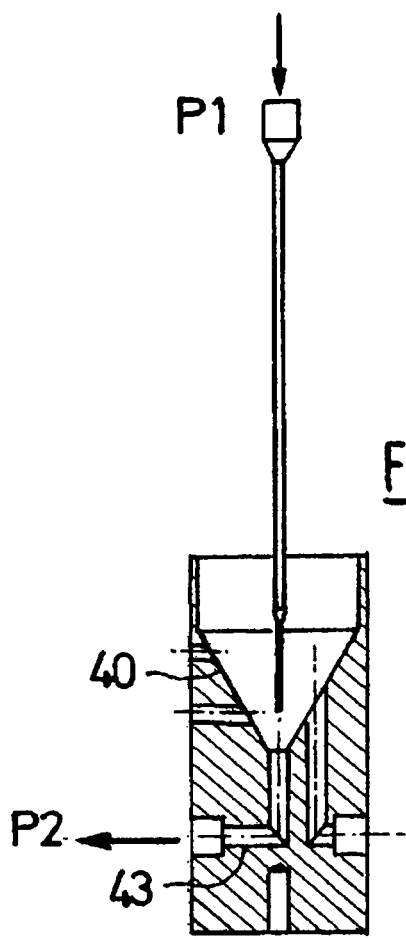
Figure 12:
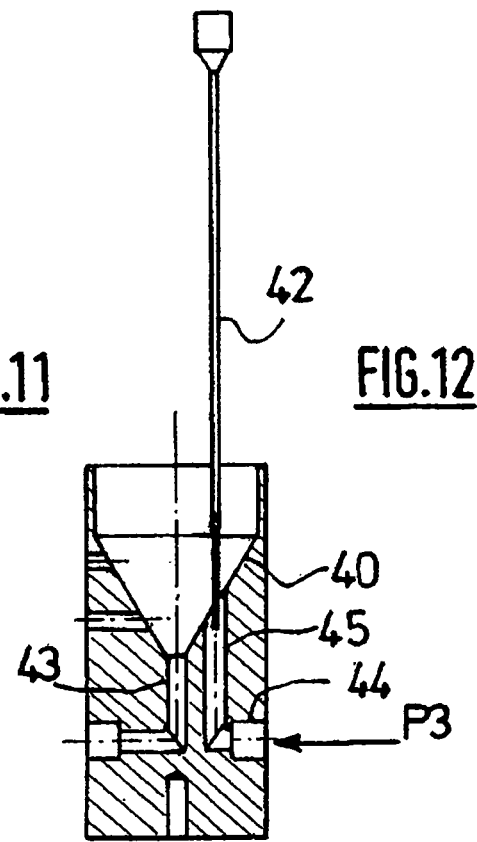
Figure 15:
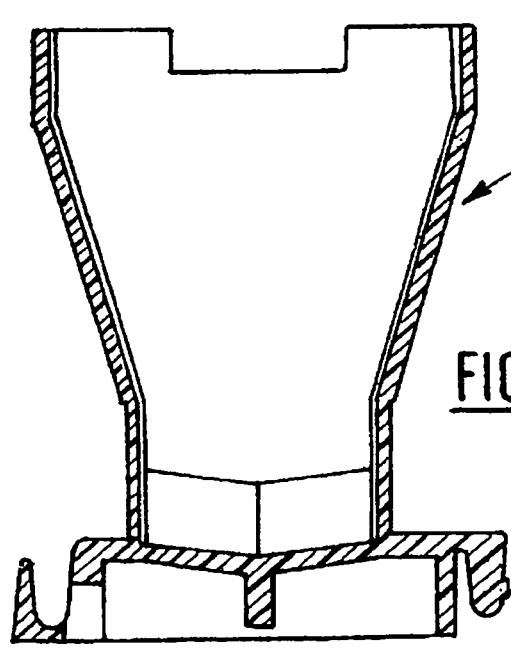
Figure 16:
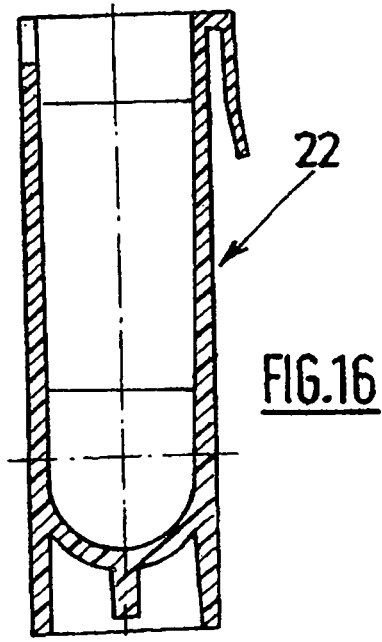
Figure 13:
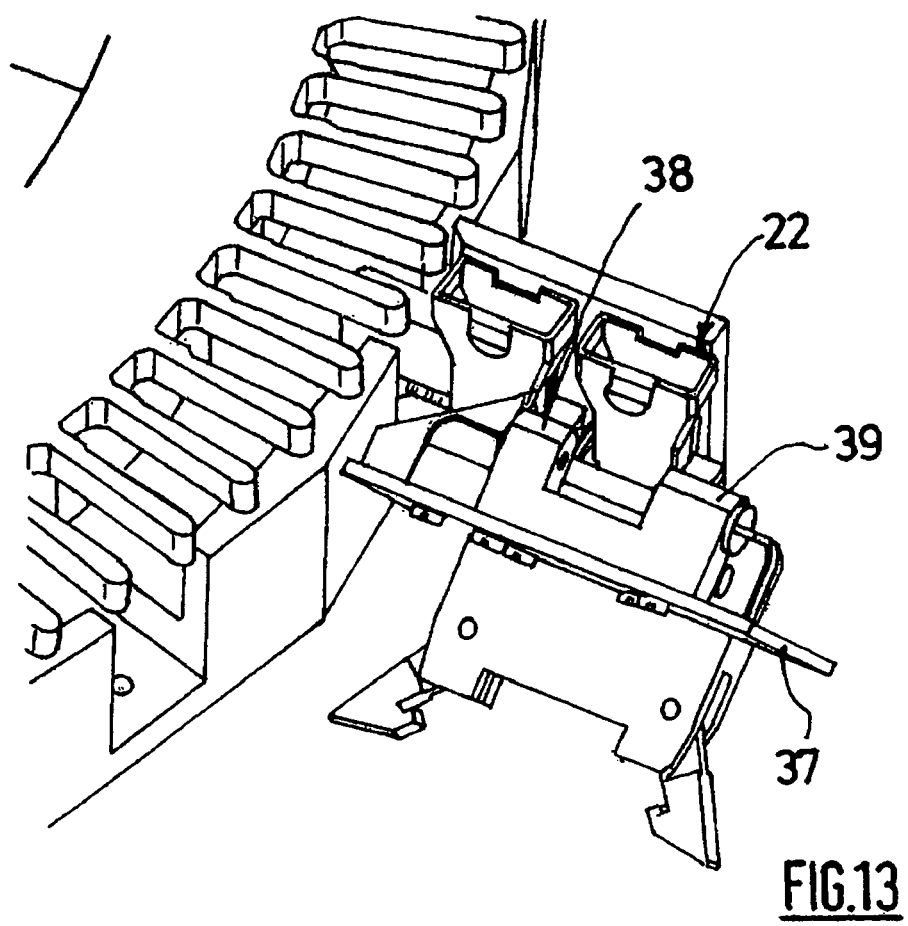
Figure 14:
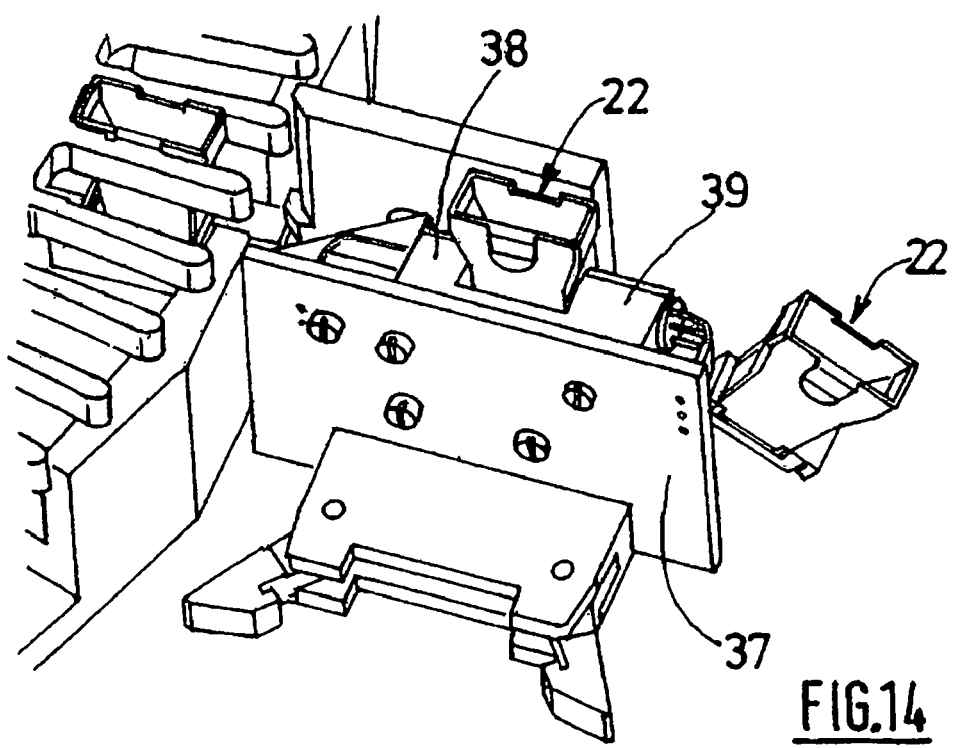

FIG. 1 is a schematic perspective view of the whole assembly,

FIG. 2 is a schematic perspective view of the cuvette drive part and the modules arranged around it, FIG. 3 is a perspective view of the cuvette drive crown wheel and of the means for guiding said cuvettes, FIG. 4 is a perspective view of a cuvette, FIG. 5 is a perspective view of several assembled cuvettes, FIG. 6 is a perspective view of a cuvette inserted into a cavity of the drive crown wheel, FIG. 7 is a perspective view of an actuator, FIG. 8 is a perspective view of a stack of cuvette plates and of the kinetics for detaching the cuvettes from one another, FIG. 9 is a perspective view of the cuvette magazine, FIG. 10 is a perspective view, on an enlarged scale, of the part of the cuvette magazine that introduces a cuvette into a cavity of the drive crown wheel, FIG. 11 is a sectional view of a rinsing well comprising a needle in a first position, FIG. 12 is a sectional view of a rinsing well comprising a needle in a second position, FIG. 13 is a perspective view of a coagulation module in a first position, FIG. 14 is a perspective view of a coagulation module in a second position, FIG. 15 is a sectional side view of a cuvette, FIG. 16 is a cross-sectional view of a cuvette.

The device according to the invention is represented schematically in FIG. 1. A computer, for example of PC type, with a keyboard, screen and conventional peripheral equipment should be added to the elements that appear in FIG. 1.

The device according to the invention comprises a first part for storing and taking samples of the specimens of biological liquid and a second part 3 for measurement and analysis. The first part 2 comprises a storage zone for the specimens of biological liquid to be analyzed, that may be a drawer with controlled or locked access with detection of the positions occupied.

The part 2 of the machine also comprises a refrigerated zone 5 for the liquid reagents in a bottle or in a container, that may be a drawer with controlled or locked access with detection of the positions occupied.

A device for reading barcode labels may also be used to read the reagent batch data.

A known device 6 for taking samples of and pipetting the specimens and the reagents makes it possible to deposit the latter into cuvettes placed in the part 3 of the device.

The part 3 of the device essentially comprises a rotor 7 mounted so as to pivot about a vertical axis, and driven by a motor (not shown). Fixed onto this rotor 7 is a drive crown wheel 8, which is a toothed crown wheel, this crown wheel delimiting radially outwardly open cavities 9. This crown wheel moves above an element 10 which has an upwardly open U-shaped cross section. The toroidally shaped piece 10 is temperature-regulated, for example at 37° C., by virtue of a known heating means such as a laminar electric resistor, a temperature sensor and an automatic control. The piece 10 therefore delimits a temperature-regulated volume between the crown wheel 8 and the U-shape in which the cuvettes are displaced under the action of the crown wheel. As emerges in particular from FIG. 3, the piece 10 comprises a certain number of openings 12 arranged at least in its outer wall, the openings 12 being arranged opposite the stations requiring introduction and/or withdrawal of the cuvettes.

As shown in FIGS. 1 and 2, a certain number of radially oriented stations are arranged around the drive crown wheel 8.

They are, in particular:
- a station 13 for the photometric measurement,
- a station 14 for evacuation of the used cuvettes to a waste container,
- a station 15 for distribution of avidin-grafted or streptavidin-grafted magnetic nanoparticles for immunocapture reactions,
- a station 16 for magnetic sedimentation and washing,
- a station 17 for developing and reading the luminescence,
- a station 18 comprising four measurement stations for the coagulation tests, that can also be used as an aliquoting or diluting station.

Stations 19 are provided for the ancillary reagents, for the magnetic particles, for the developing of the luminescence, and for the decontamination and the desorption of proteins in the tubing of the sampling system. This device also comprises a magazine 20 for the storage and the distribution of the cuvettes in the cavities of the drive crown wheel.

FIG. 4 represents a perspective view of a cuvette 22.

This cuvette is made, by molding, of a transparent plastic compatible with the various chemical, immunological and enzymatic reactions involved in the analyses. A suitable plastic is polypropylene, but any other plastic, the transparency characteristics of which for measuring optical density are sufficient and which does not have too great an affinity with proteins, may be suitable.

The cuvette has a lower part 23 of parallelepipedal shape, which provides an optical path of about 8 millimeters along the large dimension and an optical path of about 4 millimeters along the small dimension. These dimensions make it possible to obtain a minimum reaction mixture of 200 µl, which limits reagent consumptions, while at the same time maintaining optical paths that are sufficient for the spectrophotometric and turbidimetric (coagulation) measurements. The upper part 24 of the cuvette is tapered and opens out upwards so as to allow large reaction volumes, by benefiting from a wide opening, and to facilitate the rinsing of nanoparticles for the immunological tests. Thus, a cuvette 21, 22 mm in height, can contain up to 650 µl.

The cuvette comprises a bottom 21, which has a low point, as shown in FIGS. 15 and 16, such that suction makes it possible to evacuate virtually all the liquid with a very small volume remaining in the cuvette. This arrangement is advantageous for washing the magnetic particles.

As shown in the drawing, the cuvette 22 has, in its upper part 24, a downwardly turned hook 25 that projects from one of its longitudinal edges. On its other edge, the cuvette comprises a complementary recess 26. The hook 25 of a cuvette therefore covers over the recess 26 of an immediately neighboring cuvette, so as to attach two cuvettes, as shown in FIG. 5. The hook 25 also has another function, as shown in FIG. 6. Specifically, the width of the cuvette, including the hook 25, is equal to the width of a cavity 9 of the drive crown wheel. As a result, when the cuvette is introduced into the drive crown wheel, the hook 25 is applied against the wall of the cavity and, by virtue of a spring effect, immobilizes it, such that it does not move while the rotor and the crown wheel are rotating and thus allows stable optical measurements.

The base of the cuvette 22 comprises, along the direction of the width, two rims 27, 28, one, 27, of the rims forming an upwardly open hook and the other, 28, forming a downwardly open hook. The hooks 27 and 28 of two neighboring cuvettes allow them to be attached in a direction orthogonal to the direction of attachment permitted by the hooks 25.

It is therefore possible to manually or automatically produce plates of cuvettes, by carrying out an assembly in two perpendicular dimensions, as is shown in FIG. 5.

This makes it possible to store the cuvettes in a very small volume since there is no lost space between the cuvettes; thus, 160 cuvettes attached to one another can form a plate of approximately 118 mm/128 mm, which is more compact than a conventional microwell plate for determining measurements, the reaction volume of which is much smaller and which allows only vertical photometric reading with limited performance levels.

FIG. 7 represents a dual-action actuator 29 comprising an electric stepper motor, not shown on the drawing, having a screw shaft forming a cylinder, the end 30 of which is represented on the drawing, this cylinder bearing a U-shaped element 32 intended to become housed in the toroidal piece, and more specifically at an opening of this piece, in the passage for the cuvettes, so as to be able to withdraw a cuvette from the toroidal piece 10 or to reposition it therein.

FIG. 8 represents a stack of plates of cuvettes 22. The plates are superimposed. It is possible to release the lower plate 33 by displacement of the latter with respect to the other plates of the stack. Next, it is possible to free a line 32, by vertical displacement of the cuvettes of this line with respect to the other cuvettes of the same plate. Next, a cuvette 22 can be separated from the other cuvettes of the same line 34 by means of a transverse displacement.

FIGS. 9 and 10 illustrate the magazine 20 in greater detail.

As shown in FIG. 9, several plates of cuvettes are stored in the magazine. This magazine makes it possible to release the lower plate which falls onto a support. This plate is pushed to the left, until the line 34 can be shifted downwards and detached from the rest of the plate. Next, the line 34 is pushed in the direction of the drive crown wheel, after which the first cuvette is transversely released from the others by means of a push rod 35, which takes it in front of a second push rod 36, transverse to the first, that can push the cuvette 22 into a cavity 9 of the crown wheel 8 as shown in FIG. 10.

This device operates as follows.

The crown wheel 8 rotates about its vertical axis. It has a number of cavities 9 sufficient to be able to process, in parallel, the tests of the various technologies at the desired rates. 90 cavities are sufficient to process up to 400 tests/hour for biochemistry, 300 test/hour for coagulation and 150 tests/hour for immunology. The diameter of the crown wheel is approximately 250 mm, which allows the analyzer to maintain a compact nature and makes it possible to produce a "bench-top" machine that is simpler to install in a laboratory.

The magazine 20 introduces the cuvettes as described above.

The module 13 is the known spectrophotometry device. It makes it possible to carry out absorbance measurements or optical density measurements at various wavelengths. It is composed of:
- a light source, which may be a halogen lamp, a lightguide (optical fiber),
- a system for collimating the beam that passes through the cuvette to be measured, radially to the rotor in the direction of the long dimension of the cuvette. This system is inside the rotor, and more specifically the torus that acts as a track for the cuvettes,
- a photometer having means for carrying out transmitted light intensity measurements for given wavelengths, either by means of interference filters, or by using a prism and an array of photodiodes. The photometer is outside the rotor.

The module 15 is a device composed of an injection needle which is displaced vertically under the effect of an actuator. It makes it possible to introduce, into the cuvette positioned under the needle, a given volume of a solution of ancillary reagent containing streptavidin or avidin characterized magnetic nanoparticles. For this module, given the small amount of time required by the descent of the needle and by the injection of the particles, there is no need to remove the cuvettes from the rotor. In this respect, it was preferred to use generic nanoparticles grafted with avidin or with streptavidin and to produce biotinylated reagents. This solution therefore uses a single reservoir or flask of a solution containing these particles, which reservoir or flask must be periodically agitated so as to keep the particles in suspension. This flask is positioned in the zone of the ancillary reagents ANC. This solution avoids having to agitate all the immunoreagents which, without this solution of generic particles, would have to contain nanoparticles grafted with a specific antibody.

The module 16 is a device which requires the cuvette to be treated to be removed from the crown wheel, since the process is quite long and can take several tens of seconds. A small linear actuator placed inside the crown wheel and fixed onto the stationary torus therefore extracts the cuvette to be treated from the crown wheel in a centrifugal radial movement and positions it in front of magnets that attract the particles to the walls of the cuvette. The content is then suctioned out and a washing solution (ancillary reagents ANC) is introduced. The particles are resuspended by moving the cuvette out of the magnetic zone, and then by reintroducing it into the magnetic zone for a possible further washing procedure depending on the parameterization of the test under consideration. The module 16 may advantageously comprise two stations so as to be able to process two cuvettes in parallel. Once the cuvette has been processed, it is reintroduced onto the slotted rotor by means of a centripetal movement of the actuator.

The module 17 is the module for developing the luminescence. The cuvette that has been washed by the module 16 is transported by the crown wheel 8 with no specific time constraint since the reactions have been stopped. An actuator similar to that used by the module 16 extracts the cuvette from the crown wheel and, in combination with another actuator, makes it possible to introduce, by means of a vertical movement, the cuvette into the lightproof chamber. This chamber has two needles for the distribution of reagents for developing the luminescence. They are connected by pumps to the specific flasks of ancillary reagents ANC:

aqueous hydrogen peroxide conserved in an acidic medium,
sodium hydroxide solution for neutralizing and triggering the luminescence reaction.

The module 17 comprises a known photomultiplier device which makes it possible to quantify the luminescence produced after introduction of the sodium hydroxide solution. This measurement depends on the concentration of the analyte to be measured.

Once the measurement is complete, the cuvette is evacuated into the waste container by the action of the linear actuators with which the station is equipped.

The module 18 is joined together, in the case of the example, with the module 14 for evacuating the cuvettes. It is composed of several stations that can receive the cuvettes for the coagulation time measurements. Each station has a linear actuator located inside the crown wheel, fixed onto the stationary thermostatted torus that makes it possible to extract the cuvettes from the crown wheel and to position them in a measuring cell equipped with a light-emitting diode of appropriate wavelength (for example from 400 to 560 nm) or multi-wavelength component that emits a beam which passes through the cuvette along its short dimension and a photo-diode that measures the evolution of the transmitted light. When the device for processing the signal from the photo-diode observes a variation in absorbance revealing coagulation, the measuring cell can receive a new cuvette. The previous one will then be automatically pushed into the waste container. It is in this respect that the station 18 is at the same time the station 14. In fact, the calculation shows that it is not necessary to create a specific evacuation station for the cuvettes used for the biochemistry tests, and that they can pass through the coagulation stations, of which there are four in the example under consideration.

The functioning of the analyzer is described, by way of example, with a patient file X which comprises two sample tubes:

a tube of serum,
a tube of plasma.

This patient X was prescribed the following:
clinical chemistry (biochemistry): blood-glucose, cholesterol, triglycerides, CRP microlatex,
coagulation: TP, APTT,
immunology: troponin, myoglobin, TSH.

That is to say nine analyses that will be triggered sequentially but in parallel. Without going into the details of the methodologies of each analysis, let us consider the processes specific to each type of analysis: biochemistry, coagulation, immunology.

The test requests were made on the PC computer by means of the man-machine interface after or before loading of the specimens. This is preferably done using the computer connection which equips the system that takes charge of this task automatically.

The test requests are transmitted via an Ethernet link, in the example, to the processor which manages the automations and the primary processing of the results. The processor is therefore aware that, for a given specimen tube identity, a given process must therefore be carried out using, sequentially, amounts of reagents defined by their identities. The processor uses known analog and digital electronic means for accomplishing its missions.

The operator has loaded the reagents beforehand, identifying them, for example, using a barcode reader external or internal to the machine. As the specimens arrive in the laboratory, the specimen tubes are loaded into the machine, identifying them in the same way as the reagents. This is therefore the case for the two tubes of plasma and of serum originating from the same patient.

The loader 20 has already supplied the crown wheel with empty cuvettes such that they are brought to the temperature of the torus (37° C.).

For a biochemistry test: the cuvette receives specimen (serum) and reagent(s) from the sampling and pipetting system, and the photometric measurements begin and end, the cuvette remaining on the crown wheel. When the measurements are complete, the cuvette is ready to be evacuated, via one of the coagulation cells, into the waste container.

For a coagulation test: the cuvette receives specimen (plasma) and, if necessary, reagent(s) from the sampling and pipetting system. After an incubation of a few minutes, the crown wheel 8 positions the cuvette 22 under consideration opposite a coagulation station 18. The cuvette is then introduced into the measuring cell. The sampling and pipetting system then injects the triggering reagent into the cuvette. The measurement of the time begins. When the processing algorithm has detected coagulation, then the measurement is ended and a new cuvette can take the place of the used cuvette.

A used biochemistry cuvette can also take the place or a cuvette in which a dilution of the serum or of the plasma will be carried out or an aliquot of a tube will be prepared if the analyzer is equipped with a stopper-piercing device.

In fact, the accuracy of a sample taken via the needle through the stopper is insufficient for small volumes (of about 3 or 5 µl). It is therefore advisable to take a sufficient volume of, for example, 200 µl, to distribute it into an empty cuvette and then to take samples of small volumes of serum or of plasma from this cuvette.

According to a variant, a station can, of course, be dedicated to this aliquoting function.

The coagulation station is detailed in FIGS. 13 and 14, according to a variant different than that represented in FIG. 1.

In order to benefit from a signal with as great an amplitude as possible, the absorbance is read along the large dimension of the cuvette (8 mm). The cuvette must therefore be taken between the two parts of a retractable optical fork so as to allow movement of the cuvette from the rotor to the station and then from the station to the waste container.

To this effect, as represented in FIGS. 13 and 14, the coagulation station contains a plate 37 which comprises the following optical elements:
- a light-emitting diode 38 which can emit over several wavelengths in order to observe the formation of the clot by multichromatism, and detect abnormal plasmas, switched sequentially onto each of the wavelengths at times of the order of 100 msec and not supplied for measuring the ambient light reference,
- a photodiode 39 that collects the light signal transmitted through the cuvette.

The plate 37 rotates around a pivot and is equipped with a cam such that, when the cuvette that comes from the rotor is pushed by the actuator, automatically, the plate swings and the new cuvette comes into position in the measuring cell, pushing the previous cuvette into the waste bin, as represented in FIG. 14.

For an immunology test, the cuvette receives specimen and reagent(s), the crown wheel positions the cuvette under the module 15 for distributing the magnetic nanoparticles, and then the cuvette incubates for the required period of time, that may range from a few minutes to 1 hour. At the end of the incubation, the cuvette is positioned opposite the module 16 and then introduced so as to undergo therein the washing phase. The cuvette is reloaded onto the crown wheel and then positioned opposite the module 17 so as to be measured, after introduction, by luminescence. When the measurement is complete, the cuvette is evacuated into the waste container.

It can therefore be seen that all these processes can take place in parallel since each specific operation takes place outside the crown wheel in an asynchronous manner in relation to the other operations. The processor of the machine optimally manages the displacements of cuvettes with the crown wheel, which also serves as an active element for the photometric measurement.

The possibilities of inter-specimen or inter-reagent contamination are considerable, brought about by the multiplicity of the tests that can be carried out due to the multidisciplinarity. The decontamination of the sampling needle(s) must therefore be particularly well processed. Consequently, a separate rinsing and decontamination system is provided per needle. FIGS. 11 and 12 detail the rinsing wells 40 of FIG. 1.

A sampling needle 42 is connected to a pump P1 for passing given volumes of liquid from the system into the needle and the tubing. This pump can be controlled such that the flow is pulsed.

The needle 42 is positioned in the cone-shaped rinsing well 40, this well being connected, via a tube 43 that opens out at the bottom of the well, to a pump P2 which suctions the liquid expelled by the needle. Between the well 40 and the pump P2 there is a solenoid valve that can be closed when the pump P1 passes liquid from the system via the needle 42, and then opened when the pump P1 is no longer controlled. This makes it possible to close the well 40 when there is an output from the pump P1 and thus to cause the liquid to rise so as to rinse the outer walls of the needle.

The well 40 also comprises an inlet 44 of decontaminating liquid which makes it possible to neutralize the proteins that may adsorb onto the walls of the needle and of the tubing. This decontaminating liquid is part of the ancillary reagents and is delivered by a pump P3. When the process specific to each test comprises a decontamination, the needle 42 is positioned in a vertical tube 45 placed in the conical part of the well, communicating with the inlet 44 of decontaminating liquid, and dips into the decontaminating liquid, suctions out the amount required to decontaminate all the tubing to be decontaminated, and is displaced vertically and then to the center of the well where the decontaminating liquid is evacuated and the rinsing procedure using the liquid from the system is then activated.

This system makes it possible, firstly, to rinse by successive dilutions, secondly, to carry out a powerful decontamination by displacing the arm that carries the needle very little and also to automatically decontaminate the rinsing well.

Irrespective of the measurements, they are assigned to a patient identity and are transmitted to the PC which manages the man-machine interface. They are processed therein according to the calibrations, controls, etc.

Of course, the device according to the invention is not limited to the method of application described. The analyzer can thus have two sampling and pipetting systems in order to accelerate the processing of the specimens and of the reagents and to increase the rates. The system allotted to the sampling of specimens can, for example, take samples from an automated linear device for passing along tubes or from an automatic conveyor chain.

It can also be imagined that the system is equipped with a radial module for performing the measurement on the basis of another technology, for example a fluorescence module.

The cuvettes could also not be in the form of plates, without nevertheless departing from the scope of the invention.

The invention claimed is:

1. A unit cuvette for an analytical device for in vitro diagnosis comprising:
   a base,
   a lower part,
   an upper part,
   means of attachment in a first direction to at least one other unit cuvette, and
   means of attachment in a second direction, substantially perpendicular to the first direction, to at least one other unit cuvette,
   wherein:
   the means of attachment in the first direction comprise at least one hook positioned on an edge of the upper part of the unit cuvette, and
   the means of attachment in the second direction comprise two rims, a first rim forming an upwardly open hook and a second rim forming a downwardly open hook, the upwardly open hook being able to slot into the downwardly open hook of a neighboring unit cuvette, the upwardly open and downwardly open hooks being positioned on the base of the unit cuvette, along two edges of the unit cuvette orthogonal to the edge of the upper part of the unit cuvette equipped with the hook.

2. The unit cuvette as claimed in claim 1, wherein the unit cuvette is made of a transparent plastic compatible with the various reactions that the unit cuvette may receive.

3. The unit cuvette as claimed in claim 1, wherein the lower part of the unit cuvette has a parallelepipedal shape.

4. The unit cuvette as claimed in claim 3, wherein the parallelepipel lower part of the unit cuvette extends upwards by means of the upper part of the unit cuvette, the upper part of the unit cuvette being tapered and opening out upwards.

5. The unit cuvette as claimed in claim 1, comprising a cuvette bottom with a low point.

6. The unit cuvette as claimed in claim 1, wherein the means of attachment in the first direction comprise at least one downwardly open hook positioned on one of the edges the upper part of the unit cuvette.

* * * * *